United States Patent [19]

Krasnobajew

[11] 4,390,556
[45] Jun. 28, 1983

[54] MICROBIOLOGICAL TRANSFORMATIONS OF ALPHA-IONONE

[75] Inventor: Victor Krasnobajew, Küsnacht, Switzerland

[73] Assignee: Givaudan Corporation, Clifton, N.J.

[21] Appl. No.: 296,950

[22] Filed: Aug. 28, 1981

Related U.S. Application Data

[62] Division of Ser. No. 96,111, Nov. 20, 1979, Pat. No. 4,311,860.

[51] Int. Cl.³ .................... A23L 1/226; C12P 7/26; C12P 7/02
[52] U.S. Cl. ................................ 426/538; 426/534; 426/536; 252/522 R; 131/276; 568/378; 568/824; 568/447; 435/148; 435/155
[58] Field of Search .................. 252/522 R; 426/534, 426/536, 538; 131/276; 435/148, 155; 568/378, 824, 447

[56] References Cited

U.S. PATENT DOCUMENTS 4,311,860  1/1982  Krasnobajew ................. 426/534 X

OTHER PUBLICATIONS

English Translation of Japanese Kokai No. 107482/78, Derwent No. 77261A.
English Translation of Japanese Kokai No. 107497/78, Derwent No. 77268A.
English Translation of Japanese Kokai No. 107498/78, Derwent No. 77269A.
English Translation of Japanese Kokai No. 12,498/78, Derwent No. 20687.
Mikami et al., J. Agric. Biochem., 42, 1075–1077, (1978).

Primary Examiner—Joseph M. Golian
Attorney, Agent, or Firm—Robert F. Tavares

[57] ABSTRACT

Novel odorant and/or flavorant mixtures are provided by fermentation of ionone type compounds with microorganisms of the genera Botyrodiplodia, Botryosphaeria, or Lasiodiplodia.

9 Claims, No Drawings

MICROBIOLOGICAL TRANSFORMATIONS OF ALPHA-IONONE

This is a division of application Ser. No. 096,111 filed Nov. 20, 1979, now U.S. Pat. No. 4,311,860.

The present invention is concerned with a process for producing odorant and/or flavorant mixtures by the fermentation of ionone compounds with microorganisms of the genera Botryodiplodia, Botryosphaeria or Lasiodiplodia.

The ionone compounds which are subjected to the fermentation process in accordance with this invention are, suitably, compounds of the general formula

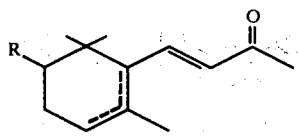

wherein R represents hydrogen or methyl and one of the dotted lines represents an additional bond.

All strains of the genera Botryodiplodia, Botryosphaeria and Lasiodiplodia, as well as variants thereof, can be used in accordance with the invention. Preferred strains are:

| | |
|---|---|
| Botryodiplodia theobromae | IFO-6469 |
| Botryosphaeria rhodina | CBS-356.59 |
| Botryosphaeria rhodina | CBS-175.26 |
| Botryosphaeria rhodina | CBS-30658 |
| Lasiodiplodia theobromae | ATCC-10936 and |
| Lasiodiplodia theobromae | ATCC-28570. |

The form in which the microorganisms are used is not critical. They can be used as the culture (suspension), i.e. including the mycelium and the corresponding nutrient solution, in the form of the mycelium or in a processed form (e.g. an enzyme extract isolated from the culture suspension or the mycelium in a manner known per se).

The culture suspension can be prepared by inoculation of a suitable medium with the microorganism. A suitable medium is one which contains carbon sources, nitrogen sources, inorganic salts and other nutrient substances suitable for the growth of the microorganism. Among the suitable carbon sources are for example, glucose, fructose, saccharose, molasses, dextrin, maltose, mannose, (e.g. maize starch), lactose and glycerine. Among the suitable nitrogen sources are, for example, nitrogen-containing organic substances such as peptone, meat extract, yeast extract, soya meal, cornsteep liquor and casein, urea, amino acids, or nitrogen-containing inorganic compounds such as nitrates and inorganic ammonium salts. Among the suitable inorganic salts are for example, phosphates of sodium, potassium, magnesium, calcium, manganese, iron and copper salts.

The cultivation of the microorganism can be carried out as a submersed culture, as a shaking culture or as a stationary culture (e.g. in fermenters). It is preferred to cultivate the microorganisms under aerobic conditions.

One suitably works in a pH-range of 3-8, preferably in the range between 4-7.5. When necessary the pH can be regulated by methods known per se, e.g. with inorganic or organic acids such as hydrochloric acid, acetic acid, oxalic acid, or bases, such as e.g. NaOH, or buffer systems such as phosphate, phthalate, tris-(hydroxymethyl)-aminomethane systems, or sugars, such as e.g. glucose.

The reaction temperature is suitably between 15° and 35° C. with a range of 24° to 32° C. being preferred.

The process in accordance with the invention is conveniently carried out by adding the compound of the general formula I as the substrate to the culture solution during cultivation or after cultivation is completed. The concentration of th substrate is suitably from 0.5 g per liter to 20 g per liter. The fermentation can be carried out by continuing under the above-mentioned conditions. The reaction time may vary depending on species and strain of the microorganism used, on the composition of the culture medium, on the substrate used and its concentration. In general, a fermentation time of 18-216 hours is sufficient and, in most cases a time of 18-144 hours, suffices. The reaction temperature generally lies between 15° and 35° C., with 24°-32° C. being preferred.

The fermentation can also be carried out using the mycelium of the microorganism isolated from the culture solution or with an enzyme extract isolated from the culture solution or the mycelium in a manner known per se. In this case, the fermentation can be conveniently carried out in aqueous solution, e.g. in a buffer solution, in physiological salt solution, in fresh nutrient solution or in water.

The substrate I can be added as such or as a solution in a hydrophilic solvent, such as acetone, dimethyl sulphoxide, methanol, ethanol, ethyleneglycol, propyleneglycol or dioxane. A surface-active agent or a dispersion agent can also be added to an aqueous suspension of the substrate, or the substrate can be emulsified by treatment with ultrasound.

Conventional anti-foam agents, namely, e.g. silicone oils (e.g. UCON), polyalkyleneglycol derivatives, maize oil or soya bean oil, can be used for the purpose of foam control.

The substrate can be added to the culture of the microorganism during the cultivation or, as mentioned above, after completed cultivation.

The point in time wherein compound I is added to the precultivated microorganism can be significant. It is desirable to achieve a growth of the microorganism which is as dense as possible (greater biomass), without permitting an over-aging of the culture which can manifest itself, for example, in sporulation and color change. If the culture is allowed to overage, it may negatively influence on the transformation of I.

The over-aging mentioned above may be avoided by methods known in the art. Microorganisms produce acids and, with many microorganisms, the pH value falls at first, approximately one-half to 2 units. This period wherein the pH drops is often followed by a period wherein the pH-value begins to rise again slowly and slightly and the biomass of the culture is still increasing. This period wherein the pH is rising is, as a rule, the best time to add the compound I.

Variations of the pH during the pre-culture depend on the microorganism used and the medium used. When certain microorganisms are used, the pH-value does not fall during the entire pre-culture, while there are other microorganisms which can lead to a pH drop of as much as 2.5 units.

Another method that can be used to determine the optimal time of adding the substrate I, in the case where the fermentation is carried out in the presence of glucose, is to determine the glucose consumption by means of a glucose analyzer. Such a determination is known to persons possessing ordinary skill in the art. This method is bases on the fact, commonly known in the art, that the experiment growth of the microorganism comes to an end when the glucose or other carbon source is consumed. Alternatively one can determine the end of the experimental growth of the microorganisms by simply weighing the biomass.

The course of the transformation of I can be followed by analytical methods known in the art, e.g. by vapor phase chromatography or thin layer chromatography. If, consequently, a considerable decrease or disappearance of I is established, more starting material, I, can then be added in order to maximize utilization of the transformation capacity of the microorganism.

The fermentation product can be isolated from the reaction mixture (i.e. the fermentation broth) by methods known per se, preferably by extraction with an organic solvent which is not miscible with water, e.g. chloroform, methylene chloride, methyl acetate, carbon tetrachloride, butanol, diethyl ether, ethyl acetate and the like. Emulsions can occur. Such emulsions can be broken up by methods known to persons of ordinary skill in the art, e.g. using filtrates such as cellite or by means of centrifugation.

The organic extraction solvent can [e.g. after drying of the extract with sodium sulfate] be removed by distillation leaving behind the product as a yellowish to brownish oil. This oil can, for purpose of decolorization be treated with active carbon. The reaction mixture can, if desired be carefully distilled under high vacuum, e.g. at pressures of 0.01 to 0.5 Torr. The transformation product can be separated into individual components, if desired, by chromatography, e.g. column chromatography, on carriers such as aluminum oxide, silica gel or cellulose.

The transformation of I can be effected by mutants of the mentioned genera and of the specifically named microorganisms. Such mutants can be obtained readily in a manner known per se, e.g. by exposing the corresponding spores or mycelium suspensions to UV-rays, X-rays or customary mutagenic substances, such as e.g. acridine orange.

The isolated mixtures obtainable in accordance with the invention represent yellowish to brownish colored liquids, are insoluble in water, but soluble in organic solvents, such as e.g. alcohols, ethers ketones, esters, hydrocarbons and halogenated hydrocarbons.

The yellowish to brownish colored liquids which are obtained are mixtures of compounds many of which are not characterized as to structure. The structure of the compounds present in such mixtures depends on the substrate used. The relative amounts of such compounds will be influenced to some extent by other factors such as the particular microorganism and reaction conditions used.

The mixtures can, however, be identified and characterized by the presence of certain compounds in these mixtures. These compounds, which are structurally related to the substrate used, can be isolated out of the mixture or their presence in such mixtures can be determined by analytical techniques, e.g. by means of gas chromatography, coupled with mass spectroscopy.

The following table presents the compounds that can be used for identification or characterization purposes.

TABLE A

| Starting Materials | Compounds present in these Mixtures |
|---|---|
| α-Ionone[a] | (1) and/or (2) |
| β-Ionone | (5) and/or (6) |
| α-Irone[b] | (7) and/or (8) |
| β-Irone | (11) and/or (12) |

FOOTNOTES TO TABLE A

[a]Compound (1) spontaneously cyclizes and dehydrates to give

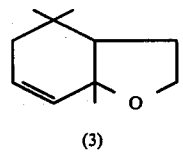

(3)

Compound (2) spontaneously cyclizes to give

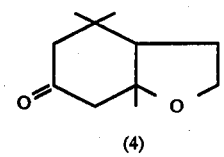

(4)

[b]Compound (7) spontaneously cyclizes and dehydrates to give

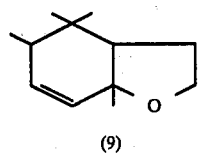

(9)

Compound (8) spontaneously cyclizes to give

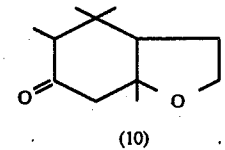

(10)

The identification can be carried by extracting the fermentation product out of the fermentation broth as described above using an organic solvent, for example ethyl acetate (3X, volume 1:1). The extract solution can be dried over sodium sulfate and the solvent removed by distillation. The remaining oil can then be dissolved in a small amount of ether-hexane (1:1) and subjected to column chromatography using silica gel (Merck) [Silica gel:oil=30:1] and ether hexane solutions as the eluting solvent, the amount of ether to hexane being steadily increased as the chromatography continues (from hexane:ether=10:1 and the final elution with pure ether). The eluting fractions can be analysed by conventional modern analytical techniques (IR, NMR, MS).

MASS SPECTRAL DATA

For spectroscopic characterization there were used samples of the fragrance mixtures which had been purified by column chromatography as described above. (Merck silica gel 60, particle size 0.063–0.2 mm, 70–230 mesh). The data are presented as follows: molecular weight (% of base peak).

Compound (1) 2-(4-hydroxy-2,6,6-trimethylcyclohex-2-en-1-yl)ethanol: 184 ($M^+$,2); 169 (15); 151 (13); 133 (14); 123 (28); 107 (23); 97 (55); 84 (100); 69 (65); 55 (34); 41 (77).

Compound (2) 2-(4-keto-2,6,6-trimethylcyclohex-2-en-1-yl)ethanol: 167 ($M^+-CH_3$,2); 164 (3): 149 (5); 138 (16); 126 (41); 109 (7); 95 (100); 83 (9); 67 (30); 55 (8); 41 (46).

Compound (3) 1,5,5-trimethyl-9-oxa-bicyclo[4.3.0]non-2-ene:
166 ($M^+$, 9); 151 (100); 107 (16); 83 (25); 55 (23); 43 (77).

Compound (4) 1,5,5-trimethyl-9-oxa-bicyclo[4.3.0]nonan-3-one: 182 ($M^+$, 1); 167 (8); 125 (100); 83 (56); 55 (35); 43 (90).

Compound (5) 2-(3-hydroxy-2,6,6-trimethylcyclohex-1-en-1-yl)ethanol: 184 ($M^+$, 24); 169 (12); 139 (100); 128 (70); 121 (23); 109 (30); 81 (18); 72 (22); 55 (15); 43 (40).

Compound (6) 2-(3-keto-2,6,6-trimethylcyclohex-1-en-1-71)ethanol: 182 ($M^+$, 2); 167 (78); 149 (18); 137 (62); 126 (80); 109 (95); 93 (55); 81 (62); 67 (68); 55 (80); 43 (100).

Compound (10) 1,4,5,5-tetramethyl-9-oxa-bicyclo[4.3.0]nonan-3-one: 196 ($M^+$, 1); 181 (51); 139 (10); 125 (100); 111 (17); 97 (14); 83 (44); 55 (34); 43 (30).

Compound (11) 2-(3-hydroxy-2,5,6,6-tetramethylcyclohex-1-en-1-yl)ethanol: 198 ($M^+$, 15); 183 (5); 153 (80); 135 (22); 128 (48); 107 (38); 95 (54); 83 (47); 72 (70); 55 (38); 43 (80).

Compound (12) 2-(3-keto-2,5,6,6-tetramethylcyclohex-1-en-1-yl)ethanol: 196 ($M^+$, 9); 181 (100); 163 (7); 151 (32); 139 (20); 126 (63); 111 (35); 97 (19); 81 (16); 69 (11); 55 (13); 41 (15).

The mixtures have particular organoleptic properties which makes them particularly suitable as odorants and/or flavorants.

The invention is also concerned with the use of these mixtures as odorants and/or flavorants.

The mixtures used in accordance with the invention can accordingly serve, for example, for the perfuming or flavoring of products, such as cosmetics (soaps, salves, powders, toothpastes, mouth washes, deodorants, shampoos, lotions eau de tiolette, Eau de Cologne, extracts, etc.), washing agents, detergents, smoking articles, etc., foodstuffs, luxury consumables and drinks, said mixtures preferably being employed in the form of compositions with other odorant or flavorants. Such odorants or flavorants which include the mixtures obtainable in accordance with the invention likewise form an object of the invention. Such compositions can be prepared by the addition of the novel mixtures of this invention to known odorant of flavoring compositions or to natural or synthetic compounds or to other mixtures suitable as ingredients of odorant or flavoring compositions.

On the basis of their valuable olfactory properties, the odorant and/or flavoring mixtures are suitable as odorants and/or flavorants, especially in combination with an extensive range of natural and synthetic odorants or flavorants such as e.g.

galbanum oil, mastix oil, vetiver oil, patchouli oil, patchouli leaf oil, sandalwood oil, cedar oil, pine oil, tree moss absolute, basil oil, mugwort oil, camomile oil, wormseed oil, celery seed oil, angelica seed oil, thyme oil, rosemary oil, lavender oil, lavandin oil, aspic oil, sage oil, aspic oil, sage oil, petitgrain oil, neroli oil, bergamot oil, lemon oil, mandarin oil, orange oil, grapefruit oil, geranium oil, benzoin resinoid, melilotus absolute, jasmine absolute, rose oil, ylang-ylang oil, corriander oil, violet leaf absolute, tuberose absolute etc., with aldehydes such as hydroxycitronellal, cyclamen aldehyde, α-hexylcinnamaldehyde, 3,5-dimethylcyclohex-3-en-1-ylcarboxaldehyde, citral, citronellal, 2,6-dimethyl-6-hepten-1-al, methylnonylacetaldehyde, undecanal, anisaldehyde etc., citronellal, 2,6-dimethyl-6-hepten-1-al, methylnonylacetaldehyde, undecanal, anisaldehyde etc., with ketones such as alpha-ionone, beta-ionone, acetanisole, 4-(para-hydroxyphenyl)-2-butanone, camphor, menthone, carvone, pulegone etc., with acetals and ketals such as phenylacetaldehyde dimethyl acetal, phenylacetaldehyde glycerine acetal, 2-methyl-1,3-dioxolan-2-ethyl acetate, capronaldehyde dimethyl acetal etc., with ethers such as eugenol methyl ether, methyl 1-methyl-cyclododecyl ether, anethol, estragol etc., with phenolic substances such as eugenol, isoeugenol, cresol etc., with alcohols, such as cis-3-hexenol, trans-2-cis-6-nonadienol, cis-6-noneol, linalool, geraniol, nerol, citronellol, nerolidol, benzyl alcohol, phenylethyl alcohol etc., with esters such as methyl dihydrojasmonate, linalyl acetate, geranyl acetate, cedryl acetate, vetiveryl acetate, para-tert.-butylcyclohexyl acetate, ortho-tert.-butylcyclohexyl acetate, benzyl acetate, benzyl salicylate, styrallyl acetate, ethyl α-methylphenylglycidate etc., with lactones such as γ-undecalactone, γ-decalactone, γ-nonalactone, δ-decalactone, δ-octalactone, coumarin etc., with acids such as lactic acid, butyric acid, α-methylbutyric acid, trans-2-hexenoic acid, trans-2-octenoic acid etc., with substances smelling musk- and amber-like such as ethylene brassylate, 4-acetyl-6-tert.-butyl-1,1-dimethyl-indane, 12-oxahexadecanolide, 8α,12-oxido-13,14,15,16-tetranorlabdane etc., with sulphur-containing compounds such as p-menthane-8-thiol-3-one, dimethyl sulphide and other sulphides and disulphides etc., with nitrogen-containing compounds such as methyl anthranilate, indole, isobutylquinoline, various pyrazines etc.

In addition to these original effects in odorant compositions, for example of the type chypre, cologne, tobacco, wood or generally flowery direction, it is also possible with the compounds of this invention to manufacture novel perfumery complexes, namely to modify the customary classical types in the direction of lighter and more lively notes.

The concentration of the mixtures obtainable in accordance with the invention, which distinguish themselves especially by their pronounced tenacity, can vary within wide limits depending on the purpose of use, for example between about 0.01 (detergents) and about 15 wt. % (alcoholic solutions). In perfume bases or concentrates the concentrations can, of course, also lie higher. The perfume bases can be used in the customary manner for the perfuming of Eau de Cologne, eau de toilette, lotions, creams, shampoos, soaps and detergents, etc.

As flavourants, the mixtures can be used, for example, for the production or improvement, intensification, enhancement or modification of fruit or berry flavours in foodstuffs (yoghurt, sweet goods, etc.); in luxury consumables (tea, etc.), drinks (lemonades etc.) and tobacco.

The pronounced flavour qualities of the mixtures make possible the use in low concentrations. A suitable dosage embraces, for example, the range of 0.1 ppm–100 ppm, preferably of 1 ppm–20 ppm in the finished product, i.e. the flavoured foodstuff, luxury consumable or drink.

In the flavouring of, for example, tobacco, the dosage can, however, also lie higher and can spread over a greater range, for example the range of 1 to 1000 ppm, preferably 5 to 500 ppm.

TABLE B

In the following Table there are compiled some effects as can be achieved in various flavours with the mixtures in accordance with the invention

| Mixture | Flavour | Dosage | Effect |
|---|---|---|---|
| B (Example II) | Raspberry | ppm in the finished product 0.1–30 ppm esp. 0.5–4 ppm | greater naturalness of the fruit character, full flavour of the ripe fruit. |
| B (Example V) | Apricot | ppm in the finished product 0.1–50 ppm esp. 0.2–5 ppm | pronounced fruitiness, more natural flavour (not only odourwise but also flavour-wise). |
| B (Example II, 5) | Tobacco | ppm in the tobacco 1–1000 ppm esp. 5–500 ppm | upon smoking more rounded-off tobacco note, besides enhancement of the tobacco flavour |

The mixture can be mixed with the ingredients used for flavouring compositions or added to such flavourants or flavouring compositions in the customary manner. Among the flavourants or flavouring compositions used in accordance with the invention there are to be understood flavouring compositions which can be diluted or dispersed in edible materials in a manner known per se. They can be converted according to methods known per se into the customary forms of use, such as solutions, pastes or powders. The products can be spray-dried, vacuum-dried or lyophilised.

For the manufacture of such customary forms of use there come into consideration, for example, the following carrier materials, thickening agents, flavour-improvers, spices and auxiliary ingredients, etc.:

Gum arabic, tragacanth, salts or brewers' yeast, alginates, carrageen or similar absorbents: maltol, spice oleoresins, smoke flavours; cloves, sodium citrate, monosodium glutamate, disodium inosine-5'-monophosphate (IMP), disodium guanosine-5-phosphate (GMP); or special flavourants, water, ethanol, propyleneglycol, glycerine.

EXAMPLES

Table I provides typical media suitable for carrying out the process of this invention and Table II provides additional information concerning typical conditions for specific fungi.

TABLE I

A. Composition of suitable growth media

| | | |
|---|---|---|
| Medium 1 | Glucose | 50.0 g |
| | Cornsteep liquor | 10.0 g |
| | KCl | 0.5 g |
| | $KH_2PO_4$ | 1.0 g |
| | $NaNO_3$ | 1.0 g |
| | Dist. water ad pH = 6.3 before sterilisation (121° C. in the autoclave) | 1000 ml, |
| Medium 2 | Glucose | 20.0 g |
| | Yeast extract | 3.0 g |
| | $NaNO_3$ | 1.0 g |
| | Glycine | 1.0 g |
| | $KH_2PO_4$ | 1.0 g |
| | $MgSO_4.7H_2O$ | 0.5 g |
| | KCl | 0.5 g |
| | $FeSO_4.7H_2O$ | 0.01 g |
| | Dist. water ad pH = 6.3 before sterilisation | 1000 ml, |
| Medium 3 | Glucose | 10.0 g |
| | Distillers solubles (vinasse of the alcohol distillation) | 10.0 g |
| | NaCl | 5.0 g |
| | $NaNO_3$ | 1.0 g |
| | $CaCO_3$ | 2.5 g |
| | Tap water ad pH = 8.0 after sterilisation | 1000 ml, |
| Medium 4 | Cornsteep liquor | 1.0 g |
| | $NH_4H_2PO_4$ | 3.0 g |
| | $CaCO_3$ | 2.5 g |
| | Soya oil | 2.2 g |
| | Yeast extract | 2.5 g |
| | Glucose | 10.0 g |
| | Dist. water ad pH = 7.6 before sterilisation | 1000 ml |
| Medium 5 | Glucose | 10.0 g |
| | Cornsteep liquor | 10.0 g |
| | Tap water ad pH = 7.2 before sterilisation | 1000 ml, |
| Medium 6 | Malt extract | 20.0 g |
| | Soya meal | 15.0 g |
| | Casein hydrolysate | 1.0 g |
| | Yeast extract | 1.0 g |
| | NaCl | 1.0 g |
| | Dist. Water ad pH = 6.3 before sterilisation | 1000 ml, |

TABLE II

B. Microorganisms (species) and growth media used

| Fungus | Culture collection No. | Bio-transformation: optimal employed amounts of I in g/l | Growth media (see Table I) |
|---|---|---|---|
| Botryodiplodia theobromae | IFO-6469 | 1–6 | 1, 2, 3, 5, 6 |
| Botryodiplodia plamarum | CBS-142.52 | 0.2–2 | 1, 6 |
| Botryosphaeria Species rhodina | CBS-356.59 | 0.5–6 | 1, 2, 3, 6 |
| " | CBS-175.26 | 1–4 | 1, 2, 3, 6 |
| " | CBS-306.58 | 1–8 | 1, 2, 3, 4, 5, 6 |
| " | CBS-230.30 | 0.5–2 | 1, 6 |
| Botryosphaeria Species rhodina | CBS-110.11 | 0.5–3 | 1, 2, 6 |
| " | CBS-374.54 | 0.5–4 | 3, 6 |
| " | CBS-124.13 | 0.5–4 | 1, 2, 4, 6 |

TABLE II-continued

B. Microorganisms (species) and growth media used

| Fungus | Culture collection No. | Bio-transformation: optimal employed amounts of I in g/l | Growth media (see Table I) |
|---|---|---|---|
| Lasiodiplodia theobromae | ATCC-9055 | 1–3 | 1, 2, 4, 6 |
| Lasiodiplodia theobromae | ATCC-10936 | 1–10 | 1, 2, 6 |
| Lasiodiplodia theobromae | ATCC-16391 | 0.5–2 | 1, 2, 6 |
| Lasiodiplodia theobromae | ATCC-28570 | 1–8 | 1, 2, 4, 5, 6 |

EXAMPLE I

Cultivation of the microorganisms

The microorganisms of the Table II are cultivated on agar plates (manufactured with medium 2). For this purpose, spores or hyphae of the respective microorganism are spread with the aid of a platinum-wire loop on the surface of the agar plates and incubated for 8–10 days at 28° C. The inoculum for the pre-cultures is manufactured by suspending the spores of these plates in 9 ml of a physiological NaCl solution and adding 1 ml of the spore suspension to 100 ml of the corresponding growth medium in a 500 ml shaking flask (Erlenmeyer flask with baffles). The flask is incubated at 28° C. for 48 hours on a rotary shaker (150–200 rpm). 8 ml of the resulting mycelium suspension are used in order to inoculate pre-cultures of 400 ml in 1 l shaking flask. After an incubation time of 24–48 hours under the above conditions, there results a dense mycelium culture (100–200 g/l of wet mycelium, when centrifuged-off at 8000 g).

Odorant composition A starting from α-ionone

A 10 l glass fermenter (Biologische Verfahrenstechnik, Basel) filled with 8 l of the sodium 1 and 1 ml of anti-foam agent UCON LB 625 is inoculated with 400 ml of a pre-culture of *Botryodiplodia theobromae* IFO-6469, grown for 24 hours on the same medium. The fermentation conditions are the following: stirring system: circulation stirrer*) (400 rpm), temperature: 28° C., aeration: 5 l air/minute. After a fermentation time of 24 hours, a dense growth of the mycelium culture (150 g of centrifuged-off moist mycelium/l [i.e.. biomass]) is attained. The pH of the culture thereby decreases from 6.3 to 5.4. At this point in time 2 g of α-ionone are added to the culture and the pH value is adjusted to pH 6.5 by means of 1-N NaOH and is held at this value with the aid of an automatic titrator during the continued fermentation. After 16-hours fermentation, the gas chromatographical analysis of a removed sample shows the disappearance of α-ionone. Thereupon, 28 g of α-ionone are added to the mass within 185 hours by means of a dosage pump, so that always ca. 5% of α-ionone, based on the product formed, is present (gas chromatographical determination). After the given time, the transformation capacity of the microorganism has largely been exhausted. Now, the fermenter content is adjusted to a pH-value of 2–3 by means of 2-N HCl and the fermentation broth is extracted with methylene chloride (threefold shaking out with 4, 1 each time). The combined extracts are dried over $Na_2SO_4$, filtered and the methylene chloride is distilled off. There are obtained 35 g of a light brownish oil with a pleasant odor after tobacco and honey. For the decolorisation, the oil in 200 ml of $CH_2Cl_2$ is treated with 10 g of animal carbon, filtered and the $CH_2Cl_2$ is removed. The odorant composition A is excellently suited as a component for tea and tobacco notes.

*(axial flow impeller with draft tube).

Identification has been carried out by mass spectrum as stated above. The composition can be characterized by the presence of compounds 1 [2-(4-hydroxy-2,6,6-trimethylcyclohex-2-en-1-yl)ethanol] and 2 [2-(4-keto-2,6,6-trimethylcyclohex-2-en-1-yl)ethanol] and especially 3 [1,5,5-trimethyl-9-oxa-bicyclo[4.3.0]non-2-ene] and 4 [1,5,5-trimethyl-9-oxa-bicyclo[4.3.0]nonan-3-one]. (See Table A).

EXAMPLE II

Odorant Composition B Starting From β-ionone

A 10 l glass fermenter (see Example 1) filled with 8 l of the medium 6 and 2 ml of anti-foam agent (polypropyleneglycol 2000) is inoculated with 400 ml of a 24 hours old pre-culture of *Botryodiplodia theobromae* IFO 6469, grown on the same medium. The conditions of the fermentation which now follows are the conditions of Example 1. After 24 hours, dense growth of the mycelium culture is attained (180 g/l). The pH-value of the culture broth thereby decreases from 6.3 to 5.2. Now, 5 g of β-ionone are added to the fermenter content, the pH-value of which is adjusted to pH 6.5 by means of 1-N NaOH and is held at this value by automatic titration. There is simultaneously connected a pump which supplies a further 30 g of β-ionone to the fermentation broth continuously within 5 days. The reaction of the β-ionone is followed gas chromatographically. After expiration of the given time, the addition of the β-ionone is discontinued and the mixture is still fermented for a further 16 hours. At this point in time only traces of β-ionone are still present. The working-up of the fermentation broth takes place analogously to Example 1. There are obtained 40.2 g of a brownish coloured oil with pleasant odour after tobacco. The oil obtained in this manner is excellently suited as a component for compositions not only of masculine but also feminine lines, e.g. for chypre or tobacco; in the latter notes rounding-off is especially attained. The oil is further usable for raspberry flavours.

The composition can be characterized by the presence of compound 5 [2-(3-hydroxy-2,6,6-trimethylcyclohex-1-en-1-yl)ethanol]. (See Table A).

EXAMPLE III

Odorant Composition B Starting From β-ionone

The manufacture of the odorant composition is effected in analogy to Example 2. However, in place of *B. theobromae* IFO 6469 there is used the microorganism *Botryosphaeria rhodina* CBS 306.58. 42 g of β-ionone are reacted and 40 g of a brownish coloured oil with pleasant tobacco odour are obtained. This transformation product of β-ionone is excellently suited as an odorant substance component in perfume compositions, see Example 2.

The composition can be characterized by the presence of compounds 5 [2-(3-hydroxy-2,6,6-trimethylcyclohex-1-en-1-yl)ethanol] and 6 [2-(3-keto-2,6,6-trimethylcyclohex-1-en-1-yl)ethanol]. (See Table A).

EXAMPLE IV

Odorant Composition B Starting From β-ionone

A 1 l Erlenmeyer flask with 4 baffles, containing 400 ml of the medium 2, is inoculated with 8 ml of a pre-culture of Lasiodiplodia theobromae ATCC 28570 and shaken at 28° C. on a rotary shaker for 24 hours (150 rpm). After this time, the culture shows a dense growth (100 g/l of moist mycelium). Now, 0.2 g of β-ionone are added to the culture and it is fermented for 16 hours while shaking. The gas chromatographical analysis of a sample (10 ml) extracted with methylene chloride shows the disappearance of β-ionone and the formation of a large number of compounds therefrom. A further 0.2 g of β-ionone are now added to the mycelium culture and it is fermented for a further 16 hours. This procedure is repeated four times. Thereupon, the flask content is acidified to a pH-value of 2 with 1-N HCl and extracted twice with 200 ml of methylene chloride each time. The combined extracts are dried over $Na_2SO_4$, the $Na_2SO_4$ is filtered off and the $CH_2Cl_2$ is distilled off. There remain 1.1 g of a yellowish oil with a pleasant odour after sweet tobacco. The obtained product is excellently suited as an odorant and/or flavourant as described under Example 2.

This composition can be characterized by the presence of compounds 5 [2-(3-hydroxy-2,6,6-trimethylcyclohex-1-en-1-yl)ethanol] and 6 [2-(3-keto-2,6,6-trimethylcyclohex-1-en-1-yl)ethanol]. (See Table A).

EXAMPLE V

Odorant Composition B Starting From β-ionone

A 70 l fermenter, containing 45 l of the medium 1 and 10 ml of anti-foam agent (polypropyleneglycol 2000), is inoculated with 1.6 l of a 24 hours old pre-culture of Lasiodiplodia theobromae ATCC 10936. The fermentation conditions are the following:

Stirring system:circulation stirrer (890 rpm), temperature: 28° C., aeration: 20 l air/minute.

After a fermentation time of 24 hours, there is attained a very dense growth of the mycelium culture (240 g of moist mycelium per liter centrifuged-off at 8000 g). The pH-value of the culture suspension thereby decreases to 5.8. At this point in time 20 g of β-ionone are added to the culture, the pH-value is adjusted to 6.2 by means of 1-N NaOH and held at this pH-value with the aid of an automatic titrator. Simultaneously, β-ionone is supplied for 4 days continuously (100 g/24 hours) by means of a pump. After completed addition, the mixture is further fermented for an additional 16 hours until only 1-2% of β-ionone are detectable gas chromatographically. The working-up of the fermenter content takes place analogously to Example 1. There are obtained 402 g of a brownish coloured oil with pleasant odour after tobacco, which is excellently suited as an odorant and/or flavourant, as mentioned under Example 2. Additionally, this odorant composition, incorporated into tobacco, especially cigarette tobacco, exhibits a remarkable flavour-enhancing effect.

The composition can be characterized by the presence of compounds 5 [2-(3-hydroxy-2,6,6-trimethylcyclohex-1-en-1-yl)ethanol] and 6 [2-(3-keto-2,6,6-trimethylcyclohex-1-en-1-yl)ethanol]. (See Table A).

EXAMPLE VI

Odorant Composition C Starting From α-irone

The manufacture of the odorant composition is effected in accordance with Example 2, with the difference that α-irone is employed in place of β-ionone. A total of 28 g of α-irone are biotransformed and there are obtained 30.2 g of a light yellow oil with pleasant flowery odour after honey and tobacco.

The composition can be characterized by the presence of compound 10 [1,4,5,5-tetramethyl-9-oxa-bicyclo[4.3.0]nonan-3-one] (See Table A).

EXAMPLE VII

Odorant Composition D Starting From β-irone

The manufacture of the odorant substance composition is effected in accordance with Example 4, with the difference that β-irone (total 1.2 g) is added in place of β-ionone to the mycelium culture of Lasiodiplodia theobromae ATCC 10936. There are isolated 1.0 g of a light brownish oil with pleasant odour after tobacco.

The composition can be characterized by the presence of compounds 11 [2-(3-hydroxy-2,5,6,6-tetramethylcyclohex-1-en-1-yl)ethanol] and 12 [2-(3-keto-2,5,6,6-tetramethylcyclohex-1-en-1-yl)ethanol]. (See Table A).

EXAMPLE VIII

Odorant Composition D Starting From β-irone

The manufacture of this odorant composition is effected in accordance with Example 1. A total of 25 g of β-irone are employed. There are isolated 26.5 g of a light brownish oil which has a pleasant odour after tobacco and is excellently suited as an odorant for compositions of this direction.

The composition can be characterized by the presence of compounds 11 [2-(3-hydroxy-2,5,6,6-tetramethylcyclohex-1-en-1-yl)ethanol] and 12 [2-(3-keto-2,5,6,6-tetramethylcyclohex-1-en-1-yl)ethanol]. (See Table A).

EXAMPLE IX

Odorant Compositions

| A | Chypre composition direction of mens lines with a content of product B | |
|---|---|---|
| | | Parts by weight |
| | Methyl 1-methylcyclododecyl ether | 200 |
| | Bergamot oil | 140 |
| | Pine-needle oil | 100 |
| | Hydroxycitronellal | 100 |
| | Citronellol | 80 |
| | Petitgrain oil | 60 |
| | Musc 174 ® Givaudan (oxa-4-pentadecanolide) | 60 |
| | Galbanum oil | 40 |
| | Coriander oil | 40 |
| | Cedarwood oil | 40 |
| | Patchouli oil | 40 |
| | Lemon oil | 40 |
| | Elemi oil | 20 |
| | | 940 |

If there are added to this conventional chypre composition for mens lines 20 parts of the product B, then this is accentuated dry. The wood notes are very pleasantly and advantageously underlined. If, however, 40 parts of the product B are added thereto, then the base is altered in the direction of tobacco. Moreover, in the novel product the elemi note which stands out somewhat in the original base is now advantageously enveloped.

| B | Perfumery base direction of chypre with a content of product B | |
|---|---|---|
| | | Parts by weight |
| Musk ambrette | | 240 |
| Phenylethyl alcohol | | 140 |
| Bergamot oil | | 100 |
| Tree moss absolute | | 60 |
| Vetivenyl acetate | | 60 |
| Jasmine synthetic | | 60 |
| Linalyl acetate | | 60 |
| Hydroxycitronellal | | 40 |
| Patchouli oil | | 30 |
| Eugenol | | 30 |
| Methyl 1-methylcyclododecyl ether | | 30 |
| Styrallyl acetate | | 30 |
| Sandela ® Givaudan (3-isocamphyl-(5)-cyclohexanol) | | 30 |
| Neroli oil | | 20 |
| Rose synthetic | | 20 |
| Castoreum synthetic | | 10 |
| C-11-aldehyde (10% in propyleneglycol) | | 10 |
| Isobutylquinoline (10% in propyleneglycol) | | 10 |
| | | 980 |

Above kind of chypre especially finds use for feminine lines. If 20 parts of the product B are added thereto, then the chypre acts substantially heavier, more rosy, a previously only weakly present amber-like, honey-like notes is intensified, which confers to the whole base a greater diffusion. The tenacity is now greater, which realises itself in the fixative properties of the novel product.

| C | Perfumery base in the direction of tea with a content of product B | |
|---|---|---|
| | | Parts by weight |
| Linalyl acetate | | 300 |
| Linalool | | 150 |
| Hydroxycitronellal | | 120 |
| Methyl 1-methylcyclododecyl ether | | 120 |
| Methyl dihydrojasmonate | | 80 |
| Patchouli leaf oil | | 60 |
| Methyleugenol | | 40 |
| Musc 174 ® Givaudan | | 30 |
| Basil oil | | 20 |
| Acetanisole | | 20 |
| Bornyl acetate | | 20 |
| Tree moss absolute | | 20 |
| | | 980 |

If there are added to this perfumery base in the direction of tea 20 parts of the product A, then it is firstly much more herby, stronger. It obtains a very fine woody-herby, dry and spicy note, which becomes remarkably impressive in the 24 h-value: The fixing properties of the product B are unmistakable. If the novel base is diluted with alcohol to 10%, as has been found for its use, the excellent combination of the methyl dihydrojasmonate with the basil oil can be established. The obtained base radiates much more warmth, also its volume has increased considerably.

| D | Perfumery base in the direction of flowery chypre with a content of product B | |
|---|---|---|
| | | Parts by weight |
| Bergamot oil | | 300 |
| Benzyl salicylate | | 100 |
| Hydroxycitronellal | | 100 |
| Geraniol | | 100 |
| Methyl dihydrojasmonate | | 90 |
| Musk ketone | | 80 |
| Benzyl acetate | | 40 |
| Patchouli oil | | 40 |
| Phenylethyl alcohol | | 40 |
| Vetivenyl acetate | | 20 |
| Musk ambrette | | 20 |
| Styrallyl acetate | | 10 |
| Galaxolide ® IFF (1,3,4,6,7,8-hexahydro-4,6,6,7,8,8-hexamethyl-cyclopenta-γ-2-benzopyran) | | 10 |
| Eugenol | | 10 |
| γ-Undecalactone | | 10 |
| Methylnonylacetaldehyde (10% in propyleneglycol) | | 10 |
| | | 980 |

If there are added to this chypre type 20 parts of the novel product B, then this is much warmer in the direction of dried fruit. This warm-fruity note, which can be used very well in compositions of direction tobacco-rose, comes into play quite especially in refined form and in a form diluted to 15%.

| E | Perfumery composition in the direction of tobacco with a content of product E | |
|---|---|---|
| | | Parts by weight |
| ortho-Tert. butylcyclohexyl acetate | | 400 |
| Jasmine synthetic | | 400 |
| Musk ketone | | 40 |
| Sandela ® Givaudan | | 40 |
| Styrallyl acetate | | 30 |
| Coumarin | | 20 |
| Isobutylquinoline (10% in propyleneglycol) | | 10 |
| Lavender oil | | 10 |
| Vetiver oil | | 10 |
| Melilotus absolute colourless | | 10 |
| Galbanum oil | | 10 |
| | | 980 |

The above tobacco composition obtains, by the addition of 20 parts of the novel product, a pronounced dried fruit-like note, which confers to the composition more volume, more vibration and a generally very interesting note. If one smells the strips after 24 hours, then the fixative properties of the novel product are very clearly detected. The coumarin note is underlined, the tobacco note acts "true".

| F | Perfumery base in the direction of tea with a content of the products A, or C | |
|---|---|---|
| | | Parts by weight |
| Bergamot oil | | 200 |
| Linalool | | 100 |
| Hydroxycitronellal | | 100 |
| Methyl 1-methylcyclododecyl ether | | 100 |
| Methyl dihydrojasmonate | | 60 |
| Patchouli leaf oil | | 60 |
| Geraniol Palmarosa | | 60 |
| Galaxolide ® IFF | | 60 |
| Methyleugenol | | 40 |
| Bergamyl acetate | | 40 |
| β-Ionone | | 40 |

| F | Perfumery base in the direction of tea with a content of the products A, or C | |
|---|---|---|
| | | Parts by weight |
| | Acetanisole | 40 |
| | Allyl-phenoxy acetate | 20 |
| | Bornyl acetate | 20 |
| | Indole (10% in propyleneglycol) | 10 |
| | Basil oil | 40 |
| | | 990 |

If there are added to this tea base 10 parts of the product A, then this acts much more spicy, the complex patchouli-basil is very pleasantly intensified and underlined, which can also be established very well in the bottom. The pronounced fixing properties of A come into play impressively.

If, however, 10 parts of the product C are added to the base, then it acts much sweeter, in the direction of honey, also here the olfactory intensification by the addition of C is ascertainable.

| G | Perfumery base in the direction of honeysuckle with a content of product A or product D | |
|---|---|---|
| | | Parts by weight |
| | Methyl dihydrojasmonate | 300 |
| | Linalool | 100 |
| | Hydroxycitronellal | 100 |
| | a-Hexylcinnamaldehyde | 80 |
| | Jasmine synthetic | 100 |
| | Acetanisole | 60 |
| | Sandela ® Givaudan | 40 |
| | Phenylethyl alcohol | 40 |
| | Benzyl acetate | 40 |
| | Benzoin resinoid Siam | 30 |
| | Linalyl antranilate | 20 |
| | Ylang-ylang oil | 20 |
| | Indole (10% in propyleneglycol) | 20 |
| | Citronellol | 20 |
| | γ-Undecalactone | 10 |
| | | 980 |

If there are added to this flowery base 20 parts of the product A, then it firstly acts much stronger, sweeter and obtains a slight honey note, which combines very well with the general honeysuckle note and passes on to this especially more olfactory volume.

A quite different effect is attainable when 20 parts of the product D are added. The base now acts fresher, lighter and there comes into play in the bottom a pleasant powdery note, which was not present in the original base. The olfactory volume is increased.

| H | Flowery base in the direction of mimosa with a content of product A or product D | |
|---|---|---|
| | | Parts by weight |
| | Terpineol | 300 |
| | Hydroxycitronellal | 240 |
| | Benzyl acetate | 60 |
| | Musk ketone | 60 |
| | Heliotropin | 60 |
| | Linalool | 40 |
| | Methyl dihydrojasmonate | 40 |
| | Bergamot oil | 40 |
| | a-Ionone | 40 |
| | Jasmine synthetic | 40 |
| | Anisaldehyde | 20 |
| | Ylang-ylang oil | 20 |
| | Eugenol | 20 |
| | | 980 |

By the addition of 20 parts of the product A the methyl dihydrojasmonate note in the above mimosa base is combined very well with the ionone note, there thus results a very soft note. This effect is still very intense when the strips are again evaluated after 24 hours.

If 20 parts of the substance D are added to the mimosa base, then this acts much fresher, cleaner in the odour, by the accentuation of the jasmine note the flowery characteristic is also emphasised.

| I | Perfumery base in the direction of hay with a content of product A or C | |
|---|---|---|
| | | Parts by weight |
| | Bergamot oil | 200 |
| | Coumarin | 100 |
| | Jasmine synthetic | 100 |
| | Phenylethyl alcohol | 100 |
| | Lavender oil | 100 |
| | Hydroxycitronellal | 60 |
| | Vetiveryl acetate | 40 |
| | Sandela ® Givaudan | 40 |
| | Musk ketone | 40 |
| | Linalool | 40 |
| | Tree moss absolute | 20 |
| | Patchouli oil | 20 |
| | Methyl salicylate | 20 |
| | Ylang-ylang oil | 20 |
| | Eugenol | 20 |
| | Indole (10% in propyleneglycol) | 10 |
| | Civet absolute (sic) (10% in propyleneglycol) | 10 |
| | | 940 |

If there are added to this hay base 60 parts of the product A, then there results from this base a harmonic rounded-off composition, the bergamot note is emphasised, which gives the odour more lightness. The product A brings about here especially a unifying effect.

If, however, 30 parts of C are added to this base, then there results in the 24 h-value a finer flowery effect, the somewhat too powdery appearing original base acts much lighter and fresher. Surprisingly, the animal slightly honey-like note of the base is accentuated by C.

| K | Perfumery base in the direction of broom with a content of product A | |
|---|---|---|
| | | Parts by weight |
| | Linalool | 200 |
| | Bergamot oil | 200 |
| | Petitgrain oil Paraguay | 200 |
| | Geranium synthetic | 100 |
| | Geraniol | 60 |
| | α-Ionone | 60 |
| | Musk ambrette | 40 |
| | Musk ketone | 40 |
| | Methyl-para-cresol | 20 |
| | Anisaldehyde | 20 |
| | Lemon oil | 20 |
| | Ylang-ylang oil | 20 |
| | | 980 |

If there are added to this base 20 parts of A, then this is immediately much stronger, more original with a pleasant spicy note. The petitgrain note is underlined slightly.

EXAMPLE X

Raspberry Flavour with the Use of Product B
(Example II)

| Components | Composition | | |
|---|---|---|---|
| | A | B | C |
| Raspberry ketone | 2.5 | 2.5 | 2.5 |
| Acetic acid 80% | 2.0 | 2.0 | 2.0 |
| Dimethylsulphide (1% in propyleneglycol) | 0.15 | 0.15 | 0.15 |
| β-Ionone (1% in propyleneglycol) | — | 1.5 | — |
| Trans-3-hexenal (50%) | 0.1 | 0.1 | 0.1 |
| Benzyl acetate | 0.3 | 0.3 | 0.3 |
| Product B (1% in ethanol) | — | — | 1.5 |

Propyleneglycol ad 100 g

Organoleptic Evaluation

The composition A (conventional raspberry base) exhibits a pleasant fruity character direction of "tutti frutti".

Composition B. If β-ionone is added to the composition A, then the fruity character of this raspberry base obtains a pleasant woody character and already now acts raspberry-like.

Composition C. If, however, the product B is added to the composition A, then the composition A obtains a pronounced raspberry odour and above all flavour, which acts extremely natural.

EXAMPLE XI

| Apricot flavour | | |
|---|---|---|
| | Parts by weight | |
| | A | B |
| Angelica root oil | 0.5 | 0.5 |
| Vanillin | 2.0 | 2.0 |
| C 16-aldehyde | 2.5 | 2.5 |
| Benzaldehyde | 2.5 | 2.5 |
| C 18-aldehyde | 5.0 | 5.0 |
| Orange oil | 5.0 | 5.0 |
| Acetic acid linalyl ester | 30.0 | 30.0 |
| C 14-aldehyde | 15.0 | 15.0 |
| Odorant composition B | — | 20.0 |
| Ethyl alcohol | 937.5 | 917.5 |
| | 1,000.0 | 1,000.0 |

By the addition of the odorant composition B (Example V) to the above composition A the impression regarding smell and regarding taste is advantageously altered, in that a pronounced fruity note, direction of dried apricot, now appears (dosage for the manufactured sugar syrup: 50 g/100 liter, diluted 1:5, i.e. 50 g of odorant composition of Example 5 in 600 liters of drink). The composition is also well suited for tobacco flavouring.

EXAMPLE XII

Use of product B in cigarette tobacco

Cigarettes were treated with a 0.5% alcoholic solution of the product B (manufactured according to Example V), and, indeed, 2 microliter were injected per cigarette. The same was repeated with a 0.25% alcoholic solution of the product B. For the organoleptic evaluation the treated cigarettes were smoked by a panel and compared with untreated cigarettes: Not only in the case of the cigarettes which were treated with a 0.5% alcoholic solution of the product B but also in the case of those which were treated with the 0.25% solution of B there was established a pronounced intensification and improvement of the tobacco flavour compared with the untreated cigarettes; moreover, the sense of feeling in the mouth was described as excellent and soft.

The strains IFO 6469, CBS 356.59, CBS 175.26, CBS 306.58, ATCC 10936 and ATCC 28570, referrd to above and in the claims were deposited or redeposited, respectively, with ATCC as follows:

| | |
|---|---|
| IFO 6469: | ATCC 20571 |
| CBS 356.59: | ATCC 20572 |
| CBS 175.26: | ATCC 20573 |
| CBS 306.58: | ATCC 20574 |
| ATCC 10936: | ATCC 20575 |
| ATCC 28570: | ATCC 20576. |

I claim:

1. A process for the manufacture of an odorant and-/or flavoring composition which comprises fermenting α-ionone with a fungus selected from the group consisting of the genera Botryodiplodia, Botryosphaeria and Lasiodiplodia under aerobic conditions wherein
   (i) the pH is between 3 and 8;
   (ii) the temperature is between 15° C. and 35° C.,
   (iii) the fermentation time is between 18 and 216 hours,
   (iv) the concentration of the substrate is from 0.5 grams per liter to 20 grams per liter, and
   (v) the fermentation product is separated from the culture by extraction.

2. A process according to claim 1 wherein the fungus is selected from the group consisting of Botyryodiplodia theobromae, Botryosphaeria rhodina and Lasiodiplodia theobromae.

3. A process according to claim 2 wherein the fungus is selected from the group consisting of Botryodiplidia theobromae IFO-6469, Botryosphaeria rhodina CBS 356.59, Botrysphaeria rhodina CBS 175.26, Botryysphaeria rhodina CBS 306.58, Lasiodiplodia theobromae ATCC 10936 and Lasiodiplodia theobromae ATCC 28570.

4. A process according to claim 2 or 3 wherein
   (i) the pH is between 4 and 7.5;
   (ii) the temperature is between 24° C. and 32° C., and
   (iii) the fermentation time is between 18 and 144 hours.

5. A mixture prepared according to the process of claim 1 which is characterized by the presence of at least one of the compounds 2-(4-hydroxy-2,6,6-trimethylcyclohex-2-en-1-yl) ethanol; 2-(4-keto-2,6,6-trimethylcyclohex-2-en-1-yl) ethanol; 1,5,5-trimethyl-9-oxabicyclo[4.3.0]non-2-ene or 1,5,5-trimethyl-9-oxa-bicyclo[4.3.0]nonan-3-one.

6. A fragrance composition comprising an olfactorily effective amount of the product of claim 5 and at least one other fragrance material.

7. A flavor composition comprising a flavor-imparting amount of the product of claim 5 and at least one other flavor material.

8. A method for improving the flavor or foodstuffs, luxury consumables and/or tobacco which comprises adding thereto a flavor imparting amount of the mixture of claim 5.

9. A method for improving the odor of fragrance compositions which comprises adding thereto an olfactorily effective amount of the mixture of claim 5.

* * * * *